(12) United States Patent
Mohammad et al.

(10) Patent No.: US 7,601,541 B2
(45) Date of Patent: Oct. 13, 2009

(54) METHOD FOR DETECTING CU CONCENTRATION OF SILICON SUBSTRATE

(75) Inventors: Shabani B. Mohammad, Tokyo (JP); Yoshikazu Shiina, Tokyo (JP)

(73) Assignee: Sumco Corporation, Tokyo (JP)

( * ) Notice: Subject to any disclaimer, the term of this patent is extended or adjusted under 35 U.S.C. 154(b) by 766 days.

(21) Appl. No.: 10/844,813

(22) Filed: May 12, 2004

(65) Prior Publication Data
US 2004/0248311 A1 Dec. 9, 2004

(30) Foreign Application Priority Data
May 12, 2003 (JP) .............................. 2003-133197

(51) Int. Cl.
*G01N 33/20* (2006.01)
(52) U.S. Cl. ........................................ 436/80; 438/471
(58) Field of Classification Search .................... 134/1; 438/14, 471; 436/80
See application file for complete search history.

(56) References Cited

U.S. PATENT DOCUMENTS

| | | | |
|---|---|---|---|
| 5,300,187 A * | 4/1994 | Lesk et al. | 438/477 |
| 5,686,314 A * | 11/1997 | Miyazaki | 436/177 |
| 2003/0104680 A1* | 6/2003 | Stefanescu et al. | 438/471 |
| 2003/0181023 A1* | 9/2003 | Kimura | 438/460 |

FOREIGN PATENT DOCUMENTS

| | | | |
|---|---|---|---|
| JP | 09064052 | * | 7/1977 |
| JP | 09064133 | * | 7/1977 |
| JP | 9-064133 | | 3/1997 |
| JP | 9-082770 | | 3/1997 |
| JP | 09-064052 | * | 7/1997 |
| JP | 09-064133 | * | 7/1997 |
| JP | 2001-196433 | | 7/2001 |

OTHER PUBLICATIONS

English language Abstract of JP 9-064133.
English language Abstract of JP 9-082770.

* cited by examiner

*Primary Examiner*—Jill Warden
*Assistant Examiner*—Dwan A Gerido
(74) *Attorney, Agent, or Firm*—Greenblum & Bernstein, P.L.C.

(57) ABSTRACT

To expediently and quantitatively estimate Cu within a silicon substrate without fully dissolving the silicon substrate and to ascertain the process contamination, there is provided a method for quantitatively determining the Cu concentration in a Cu containing silicon substrate having obverse and converse surfaces, the silicon substrate contains at least $3 \times 10^{18}$ atoms/cm$^3$ of boron and is heated at a temperature of no more than 600° C., the improvement comprises heating the converse surface of the substrate at a temperature between 300° C. to 350° C. for a period of 1 to 12 hours and then quantitatively analyze the Cu concentration at obverse and converse surfaces of the heated substrate.

4 Claims, 5 Drawing Sheets

METHOD FOR DETECTING CU CONCENTRATION OF SILICON SUBSTRATE

FIELD OF THE INVENTION

The present invention relates to a method for detecting a concentration of Cu existent within a silicon substrate doped with boron at a higher concentration. More specifically, to a method for detecting Cu at lower concentrations less than $10^{11}$ atoms/cm$^2$ existent within a silicon substrate including boron at concentrations of $3\times10^{18}$ atoms/cm$^3$ or higher.

BACKGROUND OF THE INVENTION

Among contaminating metals to be caught into a silicon substrate during oxidation and diffusion processes of the silicon substrate, Cu has an extremely high diffusion velocity and easily diffuses into the silicon substrate. The diffused Cu deteriorates the device properties, such as electric properties. It is thus important to control the thermal process so as to decrease the amount of Cu that diffuses into the silicon substrate.

To measure the concentration of Cu within such a substrate, an analysis method is primarily used by utilizing an atomic absorption spectrochemical (hereinafter called "AAS") method or a secondary ion mass spectrometric (SIMS) method. Particularly, the AAS method is capable of high sensitive analysis. However, the method utilizing the AAS method is obliged to analyze a silicon substrate by fully dissolving it in a mixed solution of hydrofluoric acid (hereinafter called "HF") and nitric acid. As such, these methods were accompanied by the following problems. Namely, it was troublesome to conduct the measurement, and further contamination might be caused during pretreatment before the measurement of the Cu in the substrate. Moreover, substrates were destroyed in either method, thereby making it impossible to use the substrates again.

Thus, the present invention proposes a method for detecting the concentration of Cu within a semiconductor substrate without destroying the semiconductor substrate (see JP-A-9-64133 (64133/1997), for example). This method is used to heat a silicon substrate at a temperature of 600° C. or lower to diffuse Cu existent within the silicon substrate and collect the Cu toward obverse and converse surfaces of the silicon substrate, and analyze the obverse and converse surfaces by a method such as the AAS method or a total reflection X-ray fluorescence analysis (hereinafter called "TXRF") method. According to this method and in case of a silicon substrate of P-type, a sufficient diffusion of Cu by heating the silicon substrate at 500° C. for 15 minutes in the atmosphere can be achieved.

Meanwhile, cleaning techniques inclusive of cleaning of a silicon substrate have been recently improved so that the concentrations of metals contaminating a silicon substrate have been lowered to about $10^{11}$ atoms/cm$^2$.

However, the P-type silicon substrate used in the method of the JP-A-9-64133 has contained boron only at a concentration of about $10^{15}$ atoms/cm$^3$, and has not been a silicon substrate doped with boron at a higher concentration. Thus, when Cu is existent within a silicon substrate at a lower concentration of less than $10^{11}$ atoms/cm$^2$ in the case of silicon substrates internally doped with boron at higher concentrations such as P$^+$ silicon substrates and P$^{++}$ silicon substrates containing boron at concentrations of $3\times10^{18}$ atoms/cm$^3$ or higher, the Cu existent within the substrate causes an electrostatic effect with the boron so that the Cu is not sufficiently diffused toward the obverse and converse surface sides of the substrate, thereby problematically deteriorating an analysis precision in estimating a concentration of Cu contained within the substrate.

SUMMARY OF THE INVENTION

It is therefore an object of the present invention to provide a method for detecting a concentration of Cu contained in a silicon substrate, capable of expediently and quantitatively estimating the Cu without fully dissolving the silicon substrate.

It is another object of the present invention to provide a method for detecting the concentration of Cu contained in a silicon substrate, for ascertaining a process contamination.

To achieve the above object, according to an embodiment of the present invention, there is provided an improved method for quantitatively determining the Cu concentration in a Cu containing silicon substrate having obverse and converse surfaces, the silicon substrate contains at least $3\times10^{18}$ atoms/cm$^3$ of boron and is heated at a temperature of no more than 600° C., the improvement comprises heating the converse surface of the substrate at a temperature between 300° C. to 350° C. for a period of 1 to 12 hours and then quantitatively analyze the Cu concentration at obverse and converse surfaces of the heated substrate.

In this detecting method, the quantitative analysis is preferably performed by an AAS method, an inductive coupling plasma mass spectrometric (hereinafter called "ICP-MS") method or a TXRF method.

Within a substrate where a large amount of boron is existent, boron has a negative electric potential and Cu has a positive electric potential. This causes an electrostatic effect, thereby causing a situation where Cu within the substrate is hardly diffused. According to the present invention, the substrate containing boron at a concentration of $3\times10^{18}$ atoms/cm$^3$ or more is heated under the conditions within the above scope, thereby making it possible to increase the diffusing amount of Cu toward the obverse and converse surface sides of the substrate. Thus, it becomes possible to expediently and quantitatively estimate the Cu diffused toward the obverse and converse surface sides without fully dissolving the silicon substrate, by quantitatively analyzing the Cu by an AAS method, an ICP-MS method or a TXRF method.

Another embodiment of the present invention is to provide a method for detecting a concentration of Cu existent within a silicon substrate, wherein the Cu existent at obverse and converse surfaces of the heated silicon substrate is dissolved in and collected into a collecting solution, and the collecting solution is quantitatively analyzed by an AAS method or a TXRF method.

By using the above method, the Cu is collected to the obverse and converse surface sides of the substrate, and the collecting solution dissolved with the obverse and converse surfaces is measured, thereby making it possible to readily measure the Cu without fully dissolving the silicon substrate.

An additional embodiment of the present invention is to provide a method for detecting a concentration of Cu existent within a silicon substrate, wherein the collecting solution is selected from the group consisting of an HF solution; a mixed solution containing HF and hydrogen peroxide; a hydrochloric acid solution; a mixed solution containing hydrochloric acid and hydrogen peroxide; a mixed solution containing hydrochloric acid and HF; an SC-1 solution; and a mixed solution containing sulfuric acid and hydrogen peroxide.

A further embodiment of the present invention is to provide a method for detecting a concentration of Cu existent within a silicon substrate, wherein the silicon substrate is divided into quadrants and then heated.

DETAILED DESCRIPTION OF THE PREFERRED EMBODIMENTS

The present invention is an improved method for quantitatively determining the Cu concentration in a Cu containing silicon substrate having obverse and converse surfaces, the silicon substrate contains at least $3 \times 10^{18}$ atoms/cm$^3$ of boron and is heated at a temperature of no more than 600° C., the improvement comprises heating the converse surface of the substrate at a temperature between 300° C. to 350° C. for a period of 1 to 12 hours and then quantitatively analyze the Cu concentration at obverse and converse surfaces of the heated substrate.

Where a large amount of boron is existent within a substrate, boron and Cu are existent in states having negative and positive electric potentials, respectively. This causes an electrostatic effect between boron and Cu, thereby causing a situation where Cu is hardly diffused. It has been thus impossible to obtain a sufficient diffusion of Cu even by heat application under the conventional conditions, when the contaminating Cu is at a lower concentration of $10^{11}$ atoms/cm$^2$ or less in a substrate containing boron at a higher concentration. However, the present invention achieves the heat application under the above-mentioned heating conditions to a substrate containing boron at a concentration of $3 \times 10^{18}$ atoms/cm$^3$ or more, thereby enabling an increased diffusing amount of Cu toward the obverse and converse surface sides of the substrate even when the concentration of contaminating Cu is low.

This will be explained in the first embodiment of the present invention.

Figure 1:
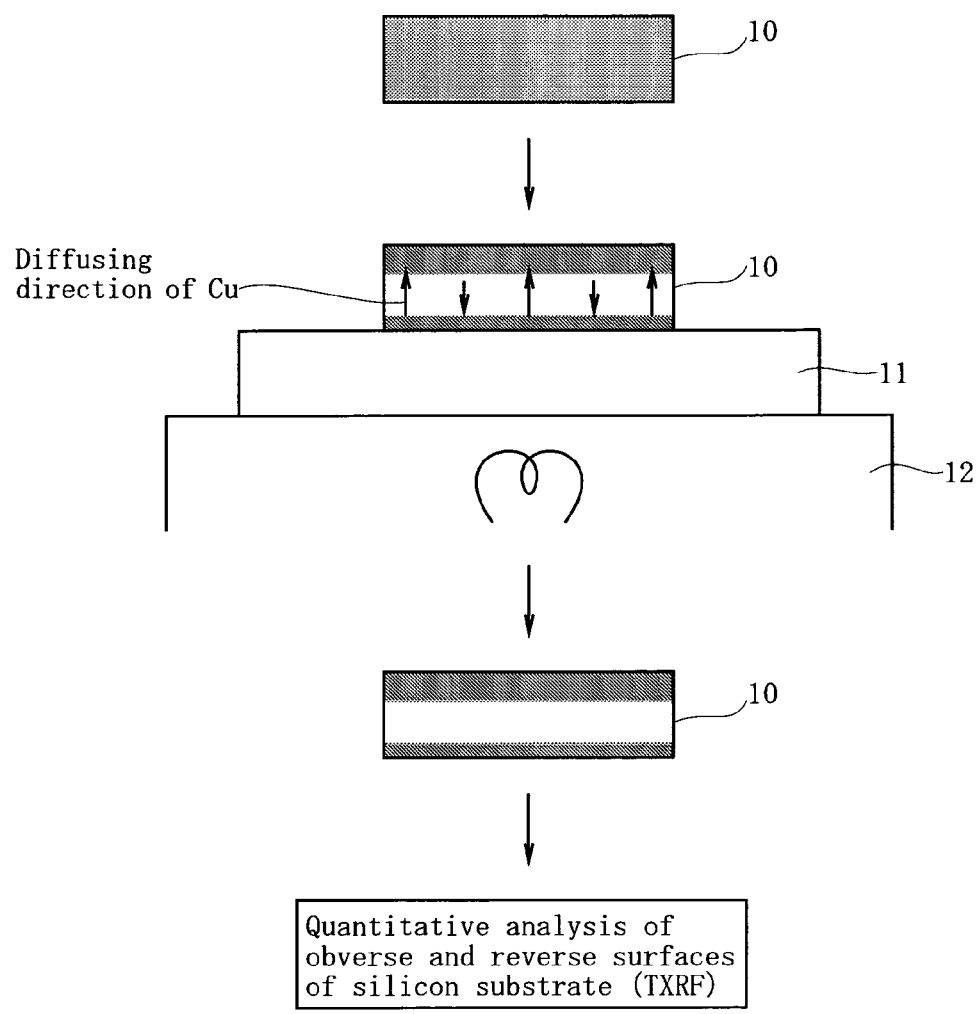
FIG. 1 is a schematic process chart showing a method for detecting a concentration of Cu existent within a silicon substrate according to a first embodiment of the present invention.

In case of a silicon wafer formed with an oxide film at its surface and being a silicon substrate which is caused with Cu contamination and that contains boron at a concentration of $3 \times 10^{18}$ atoms/cm$^3$ or more within the bulk of the substrate, the surface oxide film ($SiO_2$) is first removed by cleaning the surface by a predetermined HF aqueous solution. Concretely, the silicon substrate is immersed in an HF aqueous solution of 20 to 50 wt. % for about 10 minutes. Next, this silicon substrate 10 is placed on another clean silicon substrate 11 as shown in FIG. 1. Then the clean silicon substrate 11 is placed on a hot plate 12 (having a surface made of ceramic). Selected as the clean silicon substrate 11 is one having a diameter larger than that of the silicon substrate 10 as a measuring target. Next, the silicon substrate 10 is heated from its lower surface (converse surface) at a temperature from 300° C. inclusive to 350° C. exclusive for 1 to 12 hours in the atmosphere. When the conditions include a temperature below 300° C. and a time shorter than 1 hour in case the silicon substrate contains therein boron at a concentration of $3 \times 10^{18}$ atoms/cm$^3$ or more, Cu is not sufficiently diffused due to affection of the electrostatic effect between boron and Cu. Further, temperatures exceeding 350° C. lead to a higher solid solubility of Cu, thereby complicating detection of the Cu. Heating times longer than 12 hours fail to obtain a better result. The heating is to be preferably performed under a condition that the silicon substrate is not contaminated, such as in a clean room. It is particularly preferable to heat a silicon substrate at a temperature from 300° C. inclusive to 350° C. exclusive for about 12 hours, when the silicon substrate is contaminated by Cu at a concentration of $10^{11}$ atoms/cm$^2$ or less. When the Cu concentration is from $10^{11}$ atoms/cm$^2$ to $10^{12}$ atoms/cm$^2$, it is preferable to heat the silicon substrate at a temperature from 300° C. inclusive to 350° C. exclusive for 1 to 12 hours. When the Cu concentration exceeds $10^{12}$ atoms/cm$^2$, it is desirable to heat the silicon substrate at a temperature from 300° C. inclusive to 350° C. exclusive for about 1 hour.

Heat treatment of the silicon substrate causes 80% or more of Cu to gather at that upper surface of the silicon substrate, which is not in contact with the hot plate acting as a heating medium. In turn, less than 20% of Cu gathers at the lower surface (converse surface) of the substrate, which is in contact with the hot plate. After heat application, the obverse and converse surfaces of the silicon substrate 10 are quantitatively analyzed directly by a TXRF method, thereby making it possible to expediently and quantitatively estimate the Cu without fully dissolving the silicon substrate.

Figure 2:
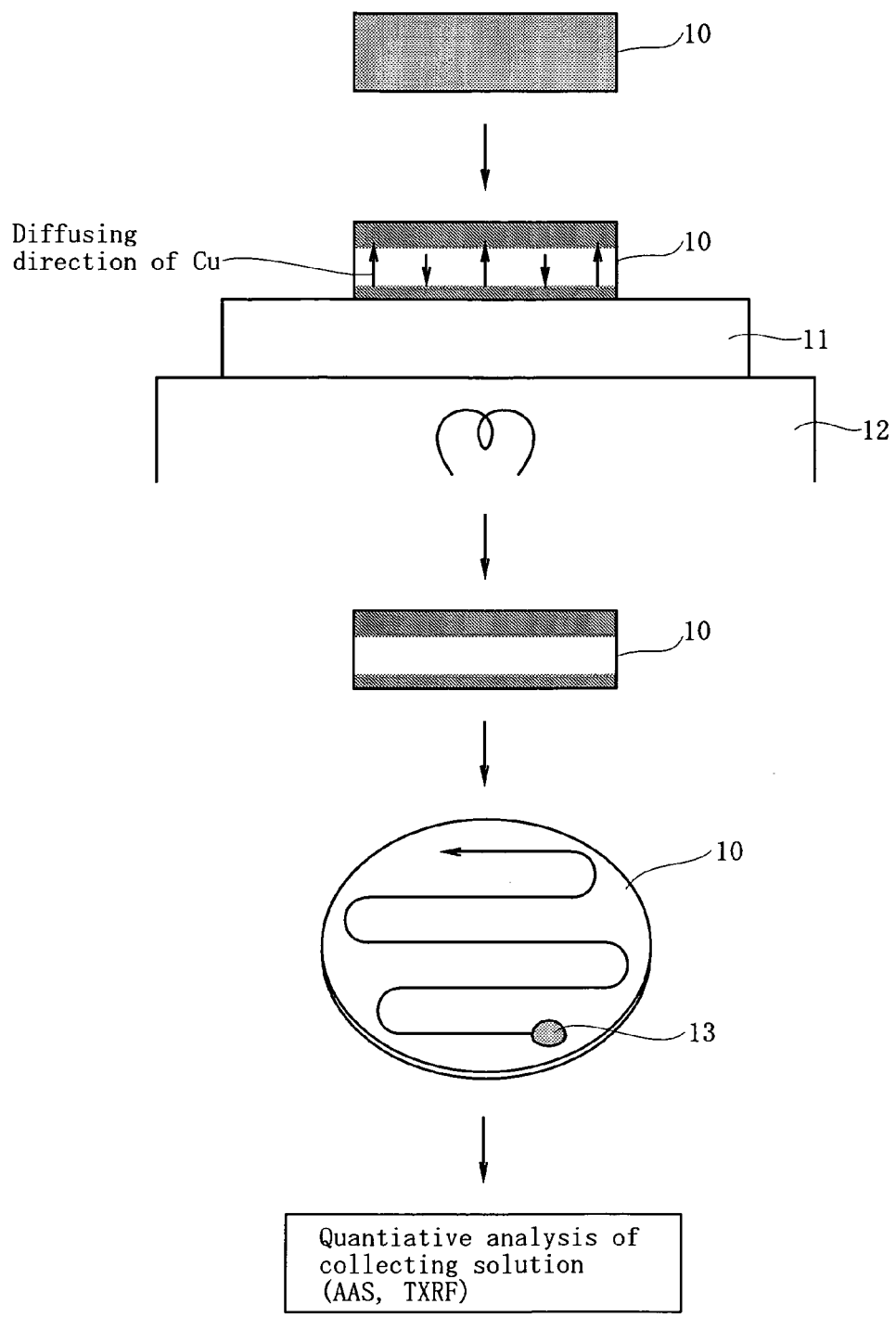
FIG. 2 is a schematic process chart showing a method for detecting a concentration of Cu existent within a silicon substrate according to a second embodiment of the present invention.

This will be explained in the second embodiment of the present invention with reference to FIG. 2. Like reference numerals in FIG. 2 are designate the same components as those in FIG. 1, respectively. This embodiment differs from the first embodiment, in the following points. Namely, Cu existent in the obverse and converse surfaces of the heated silicon substrate 10 is dissolved in and collected into a collecting solution 13, and this collecting solution 13 is quantitatively analyzed by an AAS method or a TXRF method. Those constitutions other than the above are the same as the first embodiment.

According to the second embodiment, Cu is collected onto the obverse and converse surface sides of the silicon substrate, and the Cu is measured based on the collecting solution in which the obverse and converse surfaces are dissolved to thereby collect the Cu, thereby making it possible to expediently measure the Cu without fully dissolving the silicon substrate. Preferable as the collecting method is a DE method (one Drop Etching Method). As shown FIG. 2, the DE method is conducted by dropping a few droplets of the collecting solution onto one end portion of the silicon substrate surface, such that these droplets are spread over the whole substrate surface and then collecting droplets at the opposing end portion, thereby cleaning the substrate surface and collecting metal impurities therefrom. The collecting solution is selected from an HF solution; a mixed solution containing HF and hydrogen peroxide; a hydrochloric acid solution; a mixed solution containing hydrochloric acid and hydrogen peroxide; a mixed solution containing hydrochloric acid and HF; an SC-1 solution; and a mixed solution containing sulfuric acid and hydrogen peroxide.

Figure 3:
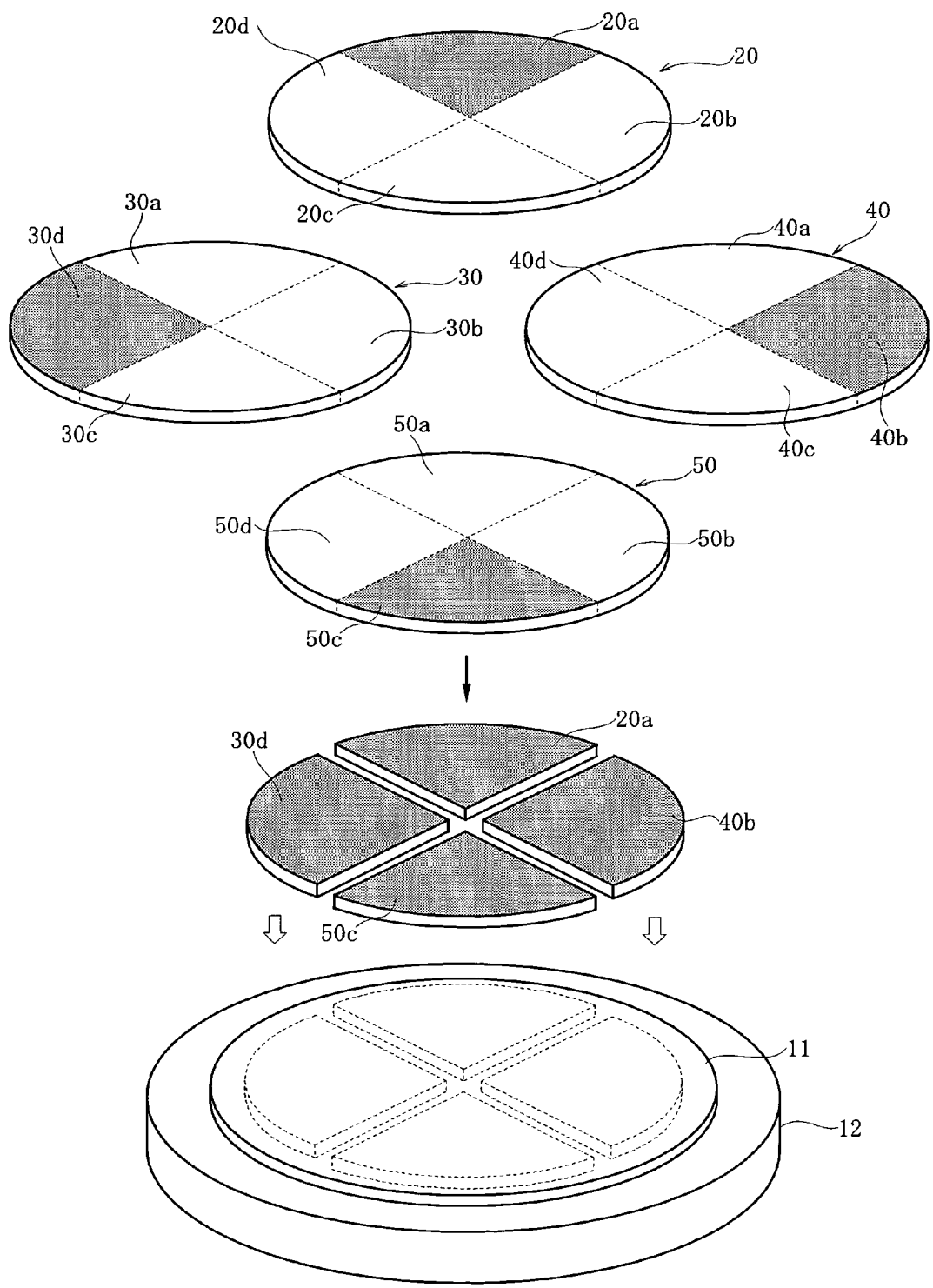
FIG. 3 is a schematic view of silicon substrates to be divided into quadrants and to be heated these quadrants, respectively.

It is also possible to divide a silicon substrate 20 into quadrants, and to heat and quantitatively analyze these quadrants. Since the division into quadrants allow the four sheets of substrates to simultaneously be placed on the hot plate, there are prepared four sheets of silicon substrates 20, 30, 40, 50 and each of them is divided into quadrants as exemplarity shown in FIG. 3. Among substrate segments 20a to 20d, 30a to 30d, 40a to 40d, 50a to 50d obtained by division in the quadrantal manner, one substrate segment (20a, 30d, 40b, 50c in FIG. 3) of each silicon substrate is placed on and heat treated by the hot plate so that the four sheets of silicon substrates are simultaneously and quantitatively analyzed, thereby enabling improvement of throughput.

EMBODIMENTS

This will be explained in the Embodiments of the present invention in detail together with Comparative Examples.

Embodiment 1

There were prepared six sheets of P$^+$ silicon substrates each provided by doping a silicon substrate with boron at a concentration of $1\times10^{19}$ atoms/cm$^3$. Each P$^+$ silicon substrate was contaminated by Cu at a predetermined concentration by a spin coating method. The contaminated substrates were heat treated under the conditions in an N$_2$ atmosphere at 900° C. for 2 hours, thereby preparing six kinds of sample substrates ("A" substrate through "F" substrate) at Cu concentrations of $2\times10^{11}$ atoms/cm$^2$, $4\times10^{11}$ atoms/cm$^2$, $5\times10^{11}$ atoms/cm$^2$, $8\times10^{11}$ atoms/cm$^2$, $1\times10^{12}$ atoms/cm$^2$ and $3\times10^{12}$ atoms/cm$^2$ within the bulks, respectively.

The prepared "A" substrate through "F" substrate were placed on hot plates via clean substrates and heated at 300° C. for 1 hour, respectively. For obverse and converse surfaces of each of the heated substrates, Cu was quantitatively analyzed by a TXRF method.

Embodiment 2

Substrates which were the same as the "A" substrate through "F" substrate of Embodiment 1 were prepared, and these substrates were placed on hot plates via clean substrates and heated at 300° C. for 12 hours, respectively. For obverse and converse surfaces of each of the heated substrates, Cu was quantitatively analyzed by an AAS method, an ICP-MS method and a TXRF method.

Comparative Example 1

Substrates which were the same as the "A" substrate through "F" substrate of the Embodiment 1 were prepared, and these substrates were placed on hot plates via clean substrates and heated at 500° C. for 15 minutes, respectively. For obverse and converse surfaces of each of the heated substrates, Cu was quantitatively analyzed by an AAS method, an ICP-MS method and a TXRF method.

Comparative Example 2

Substrates which were the same as the "A" substrate through "F" substrate of the Embodiment 1 were firstly prepared. Next, a decomposing solution containing HF, nitric acid and H$_2$SO$_4$ was filled into an accommodating container made of polypropylene (PP), and a supporting platform made of polytetrafluoroethylene was placed within the accommodating container. The supporting platform had a table positioned at a level higher than a solution level, and the "A" substrate was placed on the table. The accommodating container was then covered by a PP-made lid, and thereafter kept in a tightly closed state at a room temperature. The "A" substrate was decomposed and sublimated by holding it for about 12 hours. The decomposition residue was dropped with a mixed acid of hydrochloric acid and nitric acid to thereby dissolve the decomposition residue therein, and this solution was heated at 200° C. for 30 minutes to thereby sublimate the decomposition residue. The residue thereof was then quantitatively analyzed by the ICP-MS method. Each of the "B" substrate through "F" substrate was decomposed and sublimated by the same manner, and then quantitatively analyzed by the ICP-MS method.

Comparing Evaluation 1

Figure 4:
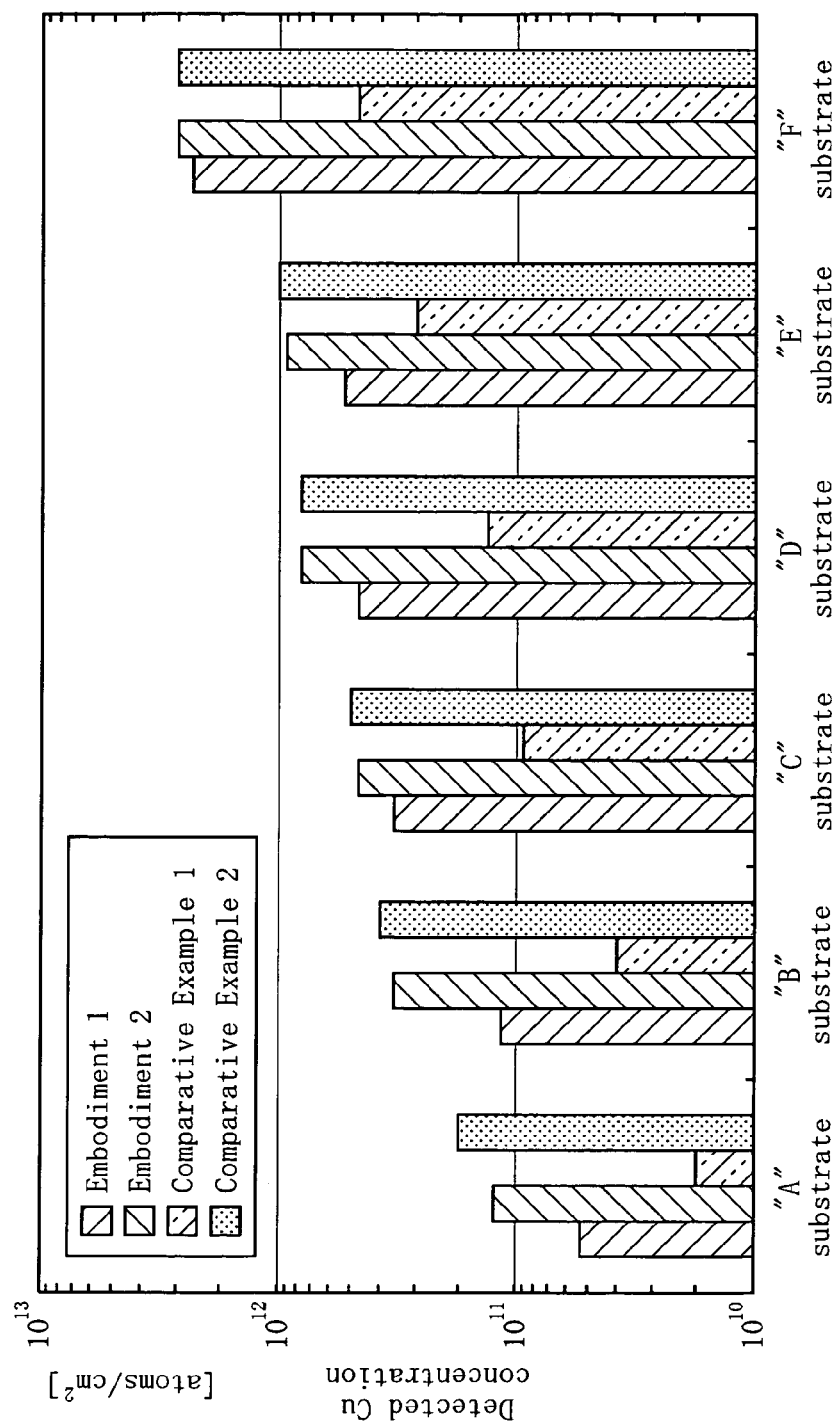
FIG. 4 is a graph showing a measurement result of detected concentrations of Cu existent within "A" substrate through "F" substrate according to Embodiments 1 and 2 and Comparative Examples 1 and 2, respectively.

FIG. 4 shows a measurement result of detected concentrations of Cu existent within the "A" substrate through "F" substrate according to Embodiments 1 and 2 and Comparative Examples 1 and 2, respectively.

As apparent from FIG. 4, the concentration of contaminating Cu was not sufficiently detected in the Comparative Example 1 which performed the heat treatment under the conditions outside the heating conditions of the present invention embracing a temperature from 300° C. inclusive to 350° C. exclusive for 1 to 12 hours. Although the Comparative Example 2, in which each silicon substrate was fully sublimated and the residue was quantitatively analyzed, is capable of sufficiently detecting the concentration of contaminating Cu, it requires a longer period of time for analysis and is thus disadvantageous from a standpoint of throughput. Contrary, each of the Embodiments 1 and 2 allowed detection of about 70% or more of the concentration of contaminating Cu.

Comparing Evaluation 2

Figure 5:
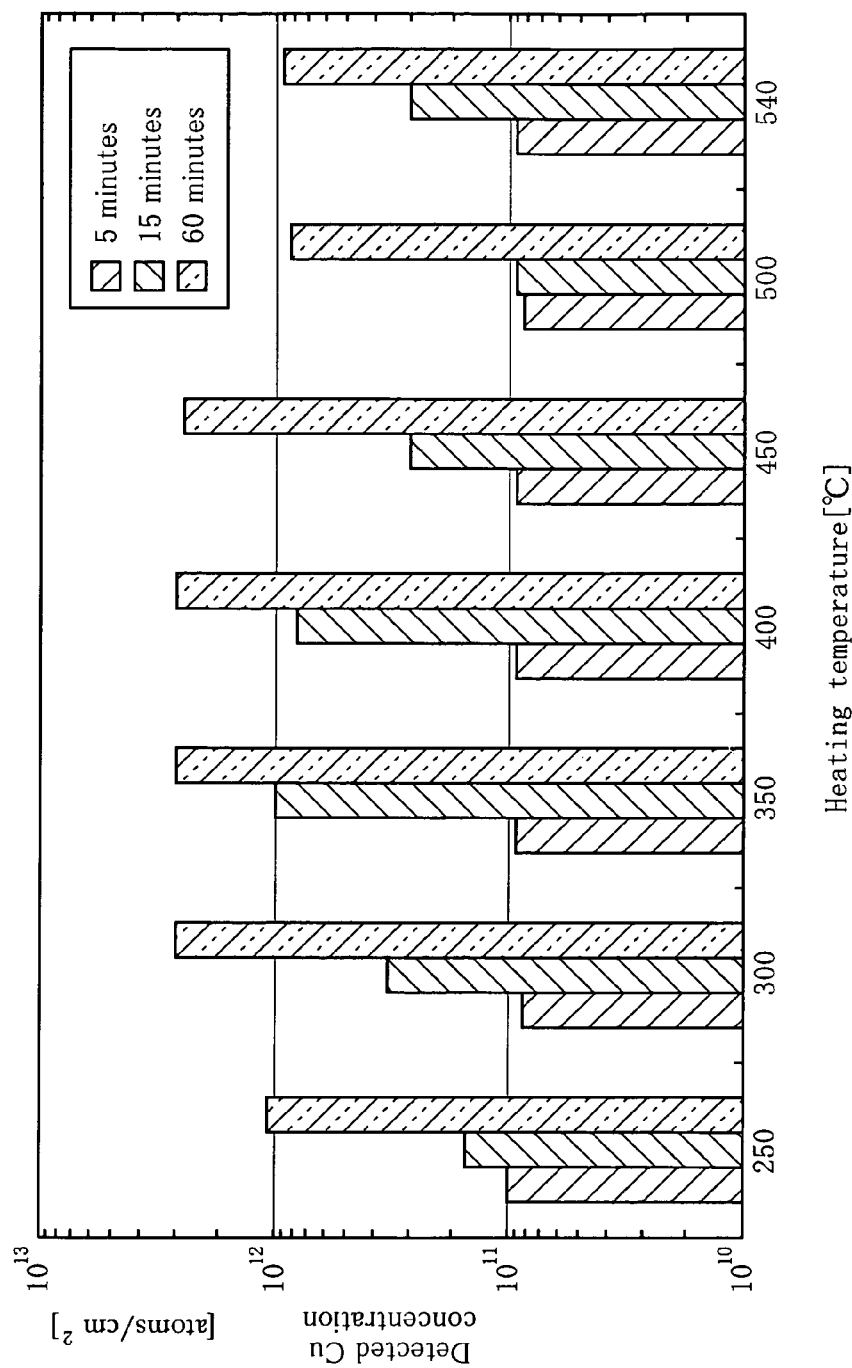
FIG. 5 is a graph showing a measurement result of detected concentrations of Cu when heat treatment conditions of comparing evaluation 2 are varied.

There were prepared 21 sheets of substrates contaminated by Cu at the same concentration as that (=$3\times10^{12}$ atoms/cm$^2$) of the "F" substrate of the Embodiment 1. These substrates were placed on hot plates via clean substrates and heated at predetermined heating temperatures for predetermined holding times, respectively. The heating temperatures were 250° C., 300° C., 350° C., 400° C., 450° C., 500° C. and 540° C., and the holding times were changed among 5 minutes, 15 minutes and 60 minutes for each heating temperature. Cu was quantitatively analyzed by the TXRF method for each of the obverse and converse surfaces of the substrates applied with the heat treatment under these conditions. FIG. 5 shows a measurement result of Cu concentrations detected from these 21 sheets of substrates.

As apparently understood from FIG. 5, there can be obtained sufficiently detected concentrations by heating and holding the substrates for 60 minutes at the heating temperatures within the range of 300° C. to 350° C., insofar as the contaminating Cu concentration is as high as $3\times10^{12}$ atoms/cm$^2$. Only the sufficiently detected concentrations were not obtained when the heating and holding times were as short as 5 minutes and 15 minutes. This is because, Cu was not sufficiently diffused toward the surfaces of the substrates for such short holding times.

As described above, the present invention is an improved method for detecting a concentration of Cu existent within a silicon substrate by heating the silicon substrate at a temperature of 600° C. or lower, and the characteristic constitution thereof is that: the substrate contains boron at a concentration of $3\times10^{18}$ atoms/cm$^3$ or more; and that the substrate is heated at a temperature from 300° C. inclusive to 350° C. exclusive for 1 to 12 hours to thereby quantitatively analyze Cu existent at obverse and converse surfaces of the heated substrate, thereby making it possible to expediently and rapidly estimate the Cu without fully dissolving the silicon substrate. It is thus possible to readily ascertain the process contamination.

Further, it is also possible to expediently and quantitatively estimate the Cu concentration, by dissolving and collecting the Cu existent at obverse and converse surfaces of the heated silicon substrate, that is dissolved in and collected into the collecting solution, and by quantitatively analyzing the collecting solution by an atomic absorption spectrochemical method or a total reflection X-ray fluorescence analysis method.

What is claimed is:

1. A method for quantitatively determining the Cu concentration in a Cu-containing silicon substrate, wherein the Cu-containing silicon substrate comprises a plurality of substrates including a first, second, third, and fourth Cu-containing silicon substrate, each of the substrates having obverse and converse surfaces and containing at least $3 \times 10^{18}$ atoms/cm$^3$ of boron by heating at a temperature of no more than 600° C., and wherein the Cu concentration in the substrate is less than $10^{11}$ atoms/cm$^2$, which comprises:

cleaving each Cu-containing silicon substrate into quadrants to obtain four quadrant sheets from each Cu-containing silicon substrate, taking a first quadrant sheet from the first Cu-containing silicon substrate, a second quadrant sheet from the second Cu-containing silicon substrate, a third quadrant sheet from the third Cu-containing silicon substrate, and a fourth quadrant sheet from the fourth Cu-containing silicon substrate, simultaneously placing the first, second, third, and fourth quadrant sheets taken from each of the first, second, third, and fourth Cu-containing substrates on a hot plate in a single layer, simultaneously heating the converse surfaces of the first, second, third, and fourth quadrant sheets at a temperature between 300° C. to 350° C. for 12 hours with the hot plate and then quantitatively analyzing the Cu concentration at the obverse and converse surfaces of each of the first, second third, and fourth quadrant sheets.

2. The method of claim 1, wherein the quantitative analysis is performed by an atomic absorption spectrochemical method, an inductive coupling plasma mass spectrometric method or a total reflection X-ray fluorescence analysis method.

3. The method of claim 1, wherein the Cu on each of the obverse and converse surfaces of the heated silicon substrate is dissolved in and collected into a collecting solution, and the collecting solution is quantitatively analyzed by an atomic absorption spectrochemical method or a total reflection X-ray fluorescence analysis method.

4. The method of claim 3, wherein the collecting solution is selected from the group consisting of a hydrofluoric acid solution; a mixed solution containing hydrofluoric acid and hydrogen peroxide; a hydrochloric acid solution; a mixed solution containing hydrochloric acid and hydrogen peroxide; a mixed solution containing hydrochloric acid and hydrofluoric acid; an SC-1 solution; and a mixed solution containing sulfuric acid and hydrogen peroxide.

* * * * *